(12) United States Patent
Schuler (10) Patent No.: US 8,781,593 B2
(45) Date of Patent: Jul. 15, 2014

(54) SYSTEM AND METHOD FOR CONTROLLING SKELETAL MUSCLES BY MEANS OF NEURO-ELECTRICAL CODED SIGNALS

(75) Inventor: Eleanor L. Schuler, Albuquerque, NM (US)

(73) Assignee: Codes of Life, LLC, Albuquerque, NM (US)

( * ) Notice: Subject to any disclaimer, the term of this patent is extended or adjusted under 35 U.S.C. 154(b) by 0 days.

(21) Appl. No.: 13/225,013

(22) Filed: Sep. 2, 2011

(65) Prior Publication Data

US 2012/0136412 A1    May 31, 2012

Related U.S. Application Data

(60) Provisional application No. 61/417,724, filed on Nov. 29, 2010.

(51) Int. Cl.
*A61N 1/36* (2006.01)
(52) U.S. Cl.
USPC .......................................................... 607/48
(58) Field of Classification Search
USPC .................................................. 607/48–49
See application file for complete search history.

(56) References Cited

U.S. PATENT DOCUMENTS

| | | | |
|---|---|---|---|
| 6,751,501 B1 | 6/2004 | Schuler et al. | |
| 6,941,171 B2 * | 9/2005 | Mann et al. | 607/39 |
| 7,308,302 B1 | 12/2007 | Schuler et al. | |
| 2004/0260360 A1 | 12/2004 | Schuler et al. | |
| 2005/0251061 A1 * | 11/2005 | Schuler et al. | 600/545 |
| 2005/0288732 A1 * | 12/2005 | Schuler et al. | 607/48 |

* cited by examiner

*Primary Examiner* — Amanda Patton
(74) *Attorney, Agent, or Firm* — Kermit D. Lopez; Luis M. Ortiz; Ortiz & Lopez, PLLC (57) ABSTRACT

A system and method for controlling a skeletal muscle by means of a neuro-electrical coded signal. An actual neuro-coded signal that is naturally generated in a body and operative in control of a skeletal muscle can be collected from a nervous network and stored in a database associated with an electronic device. An implantable muscle control device having one or more electrodes can be directly attached to an appropriate nerve leading to one or more target skeletal muscles associated with a subject. The actual neuro-coded signal can then be selected from the database and broadcasted to the implantable device associated with the subject via a neuro-code transmission approach in order to activate and regulate the affected skeletal muscles.

18 Claims, 5 Drawing Sheets

FIG. 1

Representative Muscle Neuro-Signal

SYSTEM AND METHOD FOR CONTROLLING SKELETAL MUSCLES BY MEANS OF NEURO-ELECTRICAL CODED SIGNALS

CROSS-REFERENCE TO PROVISIONAL PATENT APPLICATION

This patent application claims the benefit under 35 U.S.C. §119(e) of U.S. Provisional Application Ser. No. 61/417,724 entitled, "System and Method for Controlling Skeletal Muscles by Means of Neuro-Electrical Coded Signals," which was filed on Nov. 29, 2010 and is incorporated herein by reference in its entirety.

TECHNICAL FIELD

Embodiments are generally related to skeletal muscle control systems and methods. Embodiments are also related to neuro-electrical coded signals. Embodiments are additionally related to methods and systems for controlling a skeletal muscle by means of a neuro-electrical coded signal.

BACKGROUND OF THE INVENTION

The principal skeletal muscles with respect to the shoulder, arm, forearm, wrist, fingers, and legs associated with a human being or an animal are operated by the brain via a nerve signal. Muscle contraction and movement can be coordinated and commanded by many parts of the brain, including the cerebral cortex, cerebellum, and brainstem structures. Instructions in the form of a neuro-electrical signal travel to the muscles and cause graduated course or fine motor movements to accomplish a designated task.

Locomotion from place to place via arm, leg, and other muscular movements are common to the human and all other mammalian life. In the process of steering and directing the actions of muscles over the entire body, the brain accomplishes the duties and desires of everyday life in humans and animals. The nerves as electrically coded signals carry neuro-electrical signals, which are transmitted from the brain to a muscle to command it to contract. Such natural signals vary by the type and assemblage of neuron(s) participating in the signal. A neuron is a cell that possesses the capacity to generate a repeatable electrical signal. Signal components may vary regarding the voltage, frequency, and amplitude change to make the muscle perform its duty.

Muscles generally require a source of nutrients and oxygen, which can be supplied by the blood stream and intact nerves to carry commands. The neuro commands to the muscle occur in the form of the neuro-electrical coded signals via an efferent nerve that originate in the central nervous system (brain) and later conduct the signals on the peripheral nervous system. Biological and positional status information can be passed from the muscle to the brain by an afferent nerve to coordinate and signal that the muscle movement has been completed or is in the process of being completed. Balance and fine motor movements are the final actions and reactions that complete the task(s).

The sciatic nerve is the principal nerve for neuro-coded operation of the leg in animals and humans. Locomotion of the leg is possible via neuro-coded signals emanating from the brain, which are carried by the peripheral nerves of the sciatic and its branches. In the un-diseased and uninjured human or animal, the movement from place to place, the handling of food, tools, clothing, and other implements of daily life occurs effortlessly and as the owner of the muscles and brain desires. Motor movements can be impaired by disease, injury of muscles, or by crushed or severed nerves. Specific injuries to the brain, spinal cord or skeleton as well as lack of oxygen and other nutrients because of cardiovascular failure or damage to the respiratory tract can occur and damage muscle operation. The ability to cause muscle movement in humans or animals with spinal or other injuries make it impossible, difficult or painful to move skeletal muscles.

Based on the foregoing, it is believed that a need exists for an improved system and method for providing a normal muscular activity by means of a natural and actual neuro-electrical signal that regulate the generally smooth, ever changing symphonic patterns of muscle movement throughout life. A need also exists for an improved system and method for controlling the skeletal muscles by means of the neuro-electric coded signal, as described in greater detail herein.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for an improved skeletal muscle control system and method.

It is another aspect of the disclosed embodiments to provide for an improved system and method for controlling the skeletal muscles by means of a neuro-electric coded signal.

It is a further aspect of the disclosed embodiments to provide for an improved method and system for directly broadcasting the neuro-electric coded signal to activate and regulate the affected skeletal muscles.

The aforementioned aspects and other objectives and advantages can now be achieved as described herein. A system and method for controlling a skeletal muscle (e.g., shoulder, arm, forearm, wrist, fingers, and legs) by means of a neuro-electrical coded signal is disclosed herein. An actual neuro-coded signal that are naturally generated in a body and are operative in control of a skeletal muscle can be collected from a nervous network and stored in a database associated with an electronic device. An implantable muscle control device having one or more electrodes can be directly attached to an appropriate nerve leading to one or more target skeletal muscles associated with a subject. The actual neuro-coded signal can then be selected from the database and broadcasted to the implantable device associated with the subject via a neuro-code transmission approach in order to activate and regulate the affected skeletal muscles.

The actual neuro-coded signal can be collected from a subject (e.g., human or animal) being treated and/or from other subjects. The neuro-coded signal can be transmitted to the target area of the subject via a constant current method or a constant voltage method. In the constant current method, a positive and a negative probe (the negative probe located cranial to the positive probe) can be attached to the target nerve. The current supplied by the electronic device is consistent and repeatable throughout the delivery of the neuro-coded electrical signal and the voltage level fluctuates as the resistance changes. A ground connection can also be made between the interior muscles and an earth ground. In the constant voltage method, a signal probe can be attached to the target nerve. While the signal probe is capable of providing both the positive and negative portions of the neuro-code, only the positive portion of the neuro-code can be employed to stimulate the nerve. A ground connection is similarly made between the interior muscles and an earth ground.

The neuro-coded signals that operate a sciatic nerve associated with a leg can be recorded and utilized to activate the target muscle of the leg via the sciatic nerve. The electronic device controls the selected neuro-electric coded signals for application to the subject to adjust and control the normal skeletal muscle movements. The subject or an assistant can operate the electronic device. The frequency and amplitude of the electrical neuro-coded signals can be electrically varied so as to cause normal, fast or slow muscle movement as well as deeper or less movement in order to meet the demand of the brain.

The implantable device and the electrodes can be implanted by a surgical process to arrive in close proximity of the muscles or placed on the skin in order to transmit the codes into the muscles of the subject. Such codes can also be transmitted to the muscles via light, sound or seismic approaches. The electronic device can generate bio-responsive electrical waveforms that activate, deactivate or adjust the muscles. Such operative electrical neuro-coded signal can be reproduced in the skeletal muscles throughout the body in order to control balance locomotion, heavy lifting or the finest motor skills with respect to the subject.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

The particular values and configurations discussed in these non-limiting examples can be varied and are cited merely to illustrate at least one embodiment and are not intended to limit the scope thereof.

Natural movement with respect to a subject may require transmitting an electrically reproduced neuro waveform or coded signal into one or more muscles, including muscles throughout the entire body to control balance locomotion, heavy lifting or the finest motor skills such as, for example, threading a needle, writing information, drawing pictures with a pencil, brush or chisel on a stone tablet. The skeletal muscle control system and method described herein employs the actual naturally occurring appropriate neuro-coded signals to a human or animal muscular array located on the skeleton to activate kinetic, locomotion, fine motor skills, flight, hunting or combat efforts. Such acquired actual neuroelectrical signals can also be employed to adjust or modulate the muscle action via conduction or broadcast of the coded signals into selected nerves as represented by the arms, legs, fingers or foot. The broadcasting of the natural signals can be exerted on the necessary muscles as it relates to function(s) required by the central nervous system of humans and animals.

Figure 1:
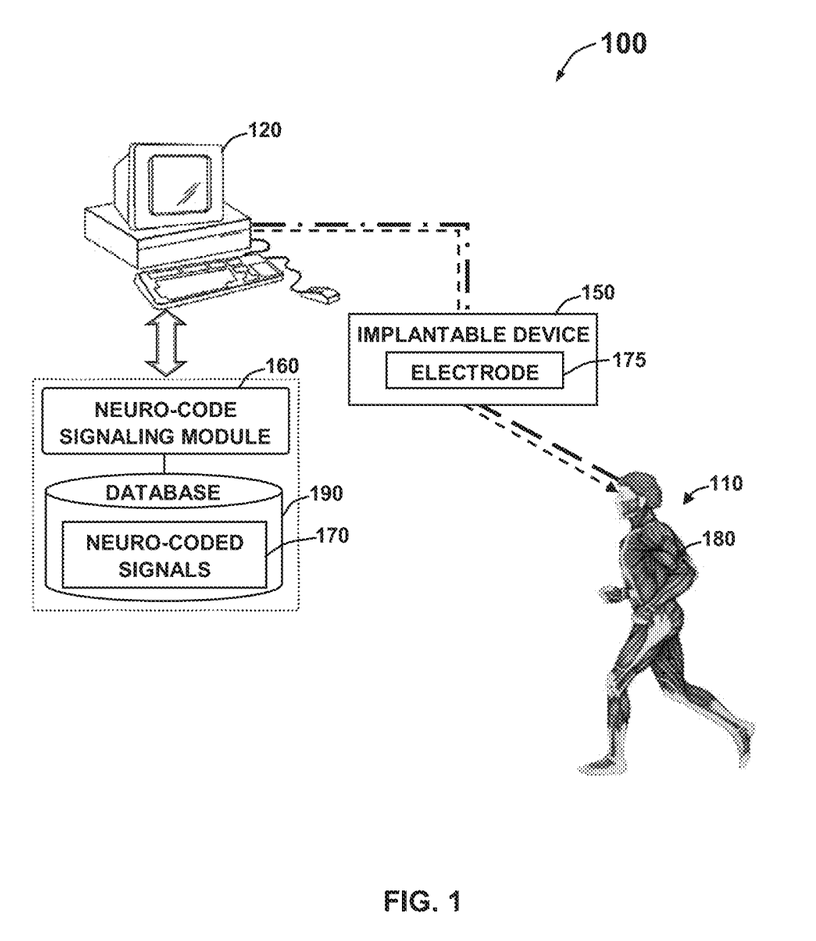
FIG. 1 illustrates a perspective view of a skeletal muscle control system associated with a subject, in accordance with the disclosed embodiments.

The skeletal muscle control system 100 generally includes an electronic device 120 associated with a neuro-code-signaling module 160 associated with a database 190. The control system 100 further includes an implantable muscle control device 150 attached with appropriate nerves leading to one or more target muscles 180 of a subject 110. The electronic device 120 can be configured to record a neuro-coded signal 170 naturally generated in a body of the subject 110 and are operative in control of the skeletal muscle 180 from a nervous network. The electronic device 120 can be a self-contained portable scientific computer or can be enslaved to a scientific computer as a system. The electronic device 120 can include a menu of operative neuro-coded signals 170 that may be cataloged in a database 190 associated with the electronic device 120. The subject 110 or an assistant in order to accomplish single or multiple muscle movements with respect to the subject 110 and thereby accomplish necessary tasks can easily operate the electronic device 120.

Note that the term "nervous network", as utilized herein, refers to a central nervous system, including the spinal cord, medulla, pons, cerebellum, midbrain, diencephalon and cerebral hemispheres, and the cranial and peripheral nervous systems, including the neurons and glia. The terms "neuro-coded signal" and "waveform signal", as utilized herein, refers to a composite electrical signal that is generated in the body and carried by neurons in the body, including neuro-codes, neuro-signals and components and segments thereof. The term "skeletal muscle", as utilized herein, refers to a striated muscle, normally having at least one attachment to the skeletal system, whose contraction and extension can be controlled or mediated by cognitive action.

The term "target muscle", as utilized herein, means and includes, without limitation, a region of the body proximal to a portion of the nervous system whereon the application of electrical signals can induce the desired neural control with the direct application (or conduction) of the signals to a target nerve. The terms "patient" and "subject", as utilized herein, refers to humans and animals. The term "plexus", as utilized herein, means and includes a branching or tangle of nerve fibers outside the central nervous system. The term "ganglion", as utilized herein, refers to a group or groups of nerve cell bodies located outside the central nervous system. The terms "skeletal muscle impairment" and "skeletal muscle disorder", as utilized herein, refer to any dysfunction of a skeletal muscle that impedes the normal function thereof. Such dysfunction can be caused by a multitude of known factors and events, including, without limitation, spinal cord injury and severance, a brain tumor, multiple sclerosis, cerebral palsy, and involuntary muscle contractions.

The neuro-coded signals 170 can be recorded by attaching an electrode 175 to a nerve associated with the subject 110, and the coded electric waveform from the nerve can be received. Note that the neuro-coded signals 170 can be acquired from the same subject to which the generated signals 170 are transmitted or a different subject. A digital converter transforms the neuro-coded signals 170 from an analog format into a digital format, which is more suitable for computer processing. The neuro-coded signals 170 can be stored in the database 190 associated with the electronic device 120 where the signals 170 can be processed, stored, adjusted, and/or broadcast, as desired. Note that the skeletal muscle control system 100 can record the operative neuro-coded signals 170 in the nerves leading to each of the skeletal muscle 180 associated with the arm, forearm wrist, hand, legs, and fingers of the subject 110.

The disclosed embodiments work by recording the signals in the nerves leading to each of the skeletal muscles associated with the arm, forearm, wrist, hand legs, and fingers in humans and animals. One example for recording the neuro-coded signals 170 that operate the skeletal muscle 180 of the subject 110 is disclosed in U.S. Pat. No. 7,308,302, entitled "Device and method to record, store and broadcast specific brain waveforms to modulate body organ functioning," which is incorporated herein by reference in its entirety. The illustration of skeletal muscles which can be controlled and regulated by the neuro-electrical coded signals 175 is disclosed in U.S. Patent Application Publication No. 20050288732, entitled "Method and system to control skeletal muscles by means of neuro-electrical coded signals," which published on Dec. 29, 2005 is also incorporated herein by reference. A further example of recording the neuron generated waveform codes is disclosed in U.S. Patent Application Publication No. 20040260360, entitled "Skeletal muscle control by means of neuro-electrical signals," which published on Dec. 23, 2004 is also incorporated herein by reference. It is understood that such patent applications represent merely non-limiting examples of some types of approaches that may be modified for use with alternative embodiments.

Figure 2:
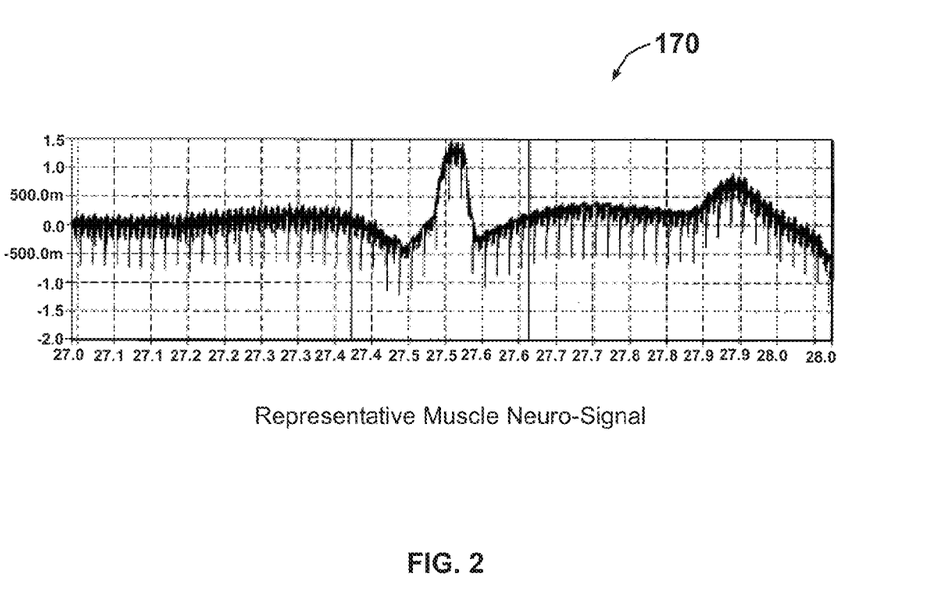
FIG. 2 illustrates an exemplary waveform signal related to a skeletal muscle operation, in accordance with the disclosed embodiments.

Referring to FIG. 2, an exemplary neuro-coded signal 170 that are operative in the control of the skeletal muscle is illustrated. The neuro-coded signal 170 generated in the body that are operative in the control of skeletal muscles 180 can be captured and transmitted to the database 190 associated with the electronic device 120. The stored signals 170 can subsequently be employed to establish at least one, preferably, multiple base-line skeletal muscle waveform signals. The implantable muscle control device 150 in association with one or more implantable electrodes 175 can be attached to the nerves (e.g., sciatic nerve) leading to the target muscles 180 of the subject 110.

The neuro-code signaling module 160 can be employed to select the actual neuro-coded signal 170 from the database 190 and broadcast to the implantable device 150 associated with the subject 110 via a constant current or constant voltage method in order to activate and regulate the affected skeletal muscles 180. The implantable muscle control device 150 is in direct contact with the body and receives the neuro-coded signal 170 from the signaling module 160. The signaling module 160 permits the electronic device 120 to regulate the signal transmission into the body. The signaling module 160 and the implantable muscle control device 150 can be entirely separate elements allowing the device to be operated remotely.

The signaling module 160 can be unique, or can be any conventional device which can provide neuro-coded signals 170 for transmission to the implantable muscle control device 150. Note that as utilized herein, the term "module" may refer to a physical hardware component and/or to a software module. In the computer programming arts, such a software "module" can be implemented as a collection of routines and data structures that performs particular tasks or implements a particular abstract data type. Modules of this type are generally composed of two parts. First, a software module may list the constants, data types, variable, routines, and so forth that can be accessed by other modules or routines. Second, a software module can be configured as an implementation, which can be private (i.e., accessible only to the module), and which contains the source code that actually implements the routines or subroutines upon which the module is based.

Therefore, when referring to a "module" herein, reference is generally made to such software modules or implementations thereof. The methodology described herein can be implemented, for example, as a series of such modules or as a single software module. Such modules can be utilized separately or together to form a program product that can be implemented through signal-bearing media, including transmission media and recordable media. The present invention is capable of being distributed as a program product in a variety of forms, which apply equally regardless of the particular type of signal-bearing media utilized to carry out the distribution.

Examples of signal-bearing media can include, for example, recordable-type media such as USB drives, Flash drives, hard disk drives, DVD media, CD ROMs, CD-Rs, etc., and transmission media such as digital and/or analog communication links. Examples of transmission media can also include devices such as modems, which permit information to be transmitted over standard telephone lines and/or the more advanced digital communications lines.

The implantable device 150 may be an electrode, antenna, a seismic transducer, or any other suitable form of conduction attachment for broadcasting the neuro-coded signals 170 that regulate or operate muscular function in humans or animals. The implantable device 150 can be attached to appropriate nerves, the cervical spine, the neck, or any skeletal muscles in a surgical process. Such surgery can be accomplished with a keyhole entrance in a thoracic or limb stereoscope procedure. If necessary, a thoracotomy approach may be required for more proper placement of the implantable device 150. Neuro-coded signals 170 known to modulate skeletal muscle function may then be transmitted into nerves that are in close proximity with the brain stem.

The surgical treatment may necessitate a minimal piercing of the skin in order to prevent deleterious attenuation of a low energy waveform signal by the electrical resistance of the skin. The implantable device 150 may be inserted into a body cavity or limb and may pierce the mucinous or other membranes so as to arrive in close proximity of the muscle into the cerebral cortex at a point where the normal signal would have emerged. Signals known to modulate muscle action or function may then be transmitted to the brainstem, spinal cord or parts of the mid brain itself. The electrodes 175 may also pierce the skull in any region to activate motor function by means of the actual neuro-coded signals 170. A mouth or nasal entrance to the brain cortex can be influenced as to either its afferent inputs or efferent outputs by implanting the implantable device 150 within its structure or in close proximity. The implantable device 150 may also be injectable or otherwise inserted or applied along the cervical spine or on the neck. The required muscle contraction force and rate (speed) may then be controlled by neuro-coded waveforms generated by the device.

A representative sampling of the muscles which can be controlled and regulated by neuro-electrical coded signals 175 can be, for example, muscles of the trunk such as, for example, multifidis, transverse abdominis, rectus abdominis, quadrates lumborum, iliacus, internal and external intercostals, internal and external oblique, rotators and erector spinae. The muscles of the head, face, and neck include occipitofrontails, masseter, temporalis, and sternocleidomastoideus. The muscles of the hip and thigh include quadriceps, hamstrings, adductors, Sartorius, piriformis, hip roatators, gluteus maxiurns, medius and minims, and pectineus. The muscles of the shoulder and the arm to the elbow includes levator scapulae, pectoralae, deltoids, biceps, triceps, subcapularis, infra and supraspinatae, rhomboids and trapezius, coracobrachialis, brachialis, and latisimus dorsi. The muscles of the hand and lower arm include finger digitorus extensor, supinator, finger and wrist flexors, pronator teres, and brachio radialis. The muscles of foot and leg include flexor digitorm longus, flexor hallucis longus, soleus, fibularis longus and brevis, extensor digitorum longus, extensor hallucis longus, and tibialis anterior. Note that the representative sampling of the muscles are described for purposes of clarity and specificity; however, they should not be interpreted as limiting features of the disclosed invention.

The coded signals 170 related to skeletal muscle operation and control originate in various brain structures. The waveform signals 170 can be directly transmitted into the affected muscles 180. The waveform signals 170 that control the noted skeletal muscles of the shoulder, arm, wrist, and hand can also be transmitted through the brachial plexus, and the radial, median, and ulnar nerves. The waveform signals 170 that control a target skeletal muscle or muscles 180 can be captured or collected along any of the nerves carrying the waveform signals 170 to the target skeletal muscle 180. By way of example, the waveform signals 170 transmitted to the abductor pollicis muscle of the hand can be captured from the brachial plexus.

The electronic device 120 can supply the operative neuro-coded signals 170 in the form of neuro-coded waveforms in order to permit more or less normal muscle movement in the subject 110. The operative neuro-coded signals 170 can be regenerated from an internal or external place or point of the body for medical treatment so as to cause normal and usual movement in the muscle 180 of the subject 110. The operative neuro-coded signals 170 with respect to the subject 110 can be electrically varied as to frequency and amplitude in order to cause normal, fast or slow muscle movements as well as deeper or less movements with respect to the demand of the brain of the subject 110.

Note that the neuro-coded signals 170 can also be transmitted via light, sound or seismic approaches. The neuro-coded signal 170 occurs naturally as a burst signals followed by a pause and then another burst of neuron activity followed by a pause and so it is on and on throughout life. The signal amplitude or time of pause can be varied to accomplish the muscle deed required. Muscle activity requires variable repetitive neuro-coded signals 170 as humans or animals move. Various muscles operate in symphonic pattern being conducted by the brain to accomplish the mission assigned. The adequate but variable space between the signals permits synchronization of movement into smooth actions.

Figure 3:
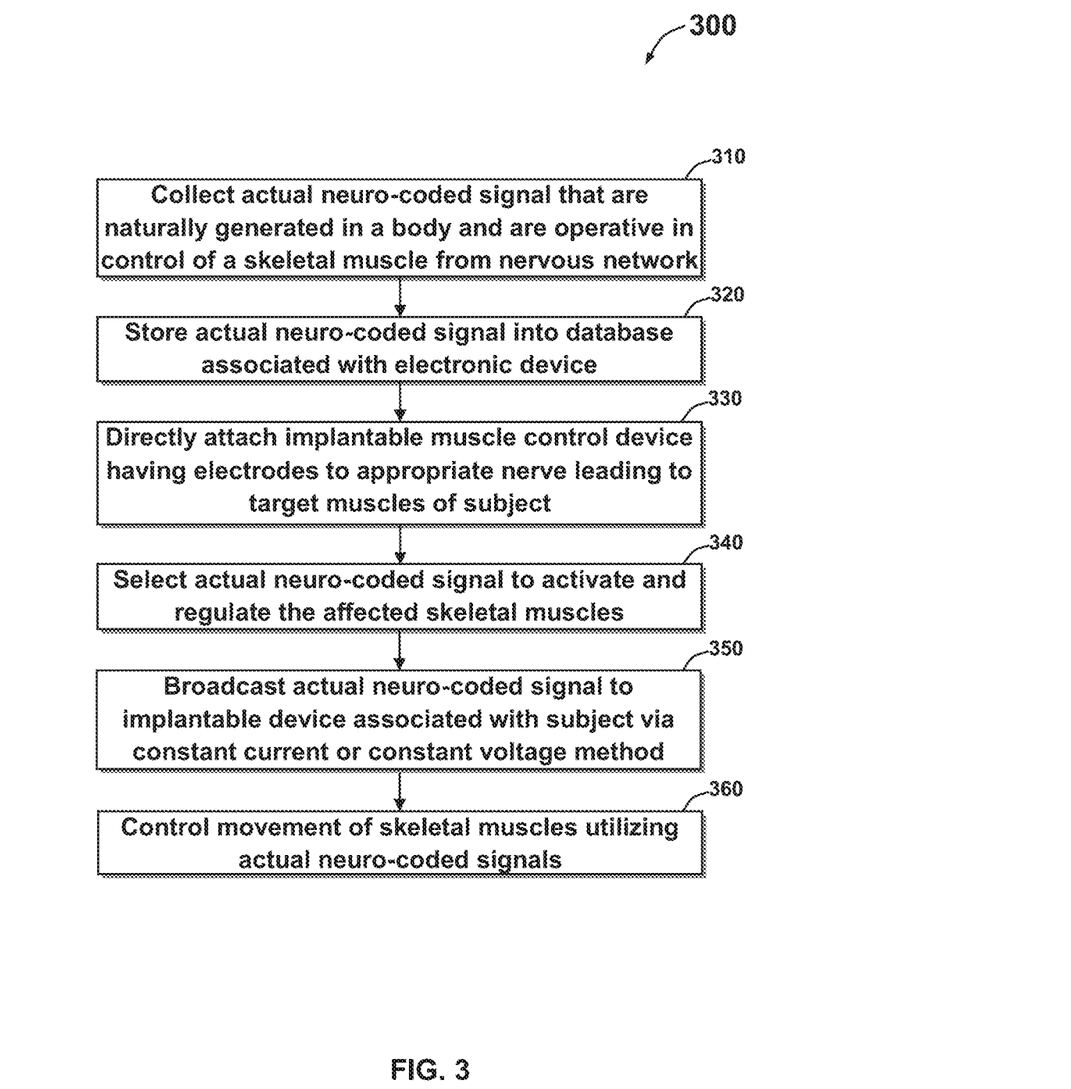
FIG. 3 illustrates a high level flow chart of operation illustrating logical operational steps of a method for controlling the skeletal muscles by means of the neuro-coded electric signal, in accordance with the disclosed embodiments.

FIG. 3 illustrates a high level flow chart of operation illustrating logical operational steps of a method 300 for controlling the skeletal muscles 180 by means of the neuro-coded signals 170, in accordance with the disclosed embodiments. Note that in FIGS. 1-6, identical or similar blocks are generally indicated by identical reference numerals. The actual neuro-coded signal 170 that are naturally generated in a body and are operative in control of a skeletal muscle can be collected from a nervous network as indicated at block 310. The actual neuro-coded signal 170 can be stored into the database 190 associated with the electronic device 120, as illustrated at block 320. The term "neuro-coded signal", as used herein, includes a composite electrical signal that is generated in the body and carried by neurons in the body including neuro-codes, neuro-signals and components, and segments thereof.

The implantable muscle control device 150 having one or more electrodes 175 can be directly attached to an appropriate nerve leading to the target muscles 180 of the subject 110, as depicted at block 330.

The actual neuro-coded signal 170 can be selected to activate and regulate the affected skeletal muscles 180, as indicated at block 340. The actual neuro-coded signal 170 can be broadcasted to the implantable device 150 associated with a subject 110 via a constant current or constant voltage method, as illustrated at block 350. The operative neuro-coded signals 170 can be bio-responsive electrical waveforms 170 that can be employed to activate, deactivate, or adjust operations of the muscles 180 associated with the subject 110.

The constant current approach requires that the current supplied by the electronic device 120 is consistent and repeatable throughout the delivery of the neuro-coded signals 170. Such approach permits the voltage level to fluctuate as the resistance changes and thereby creates a movement in the skeletal muscle 180 of the subject 110. Similarly, the constant voltage approach requires that the voltage supplied by the electronic device 120 is consistent and repeatable throughout the delivery of the neuro-coded signals 170 to the muscles 180 of the subject 110. The movement of skeletal muscles 180 can be controlled utilizing the actual neuro-coded signals 170, as depicted at block 360.

Figure 4:
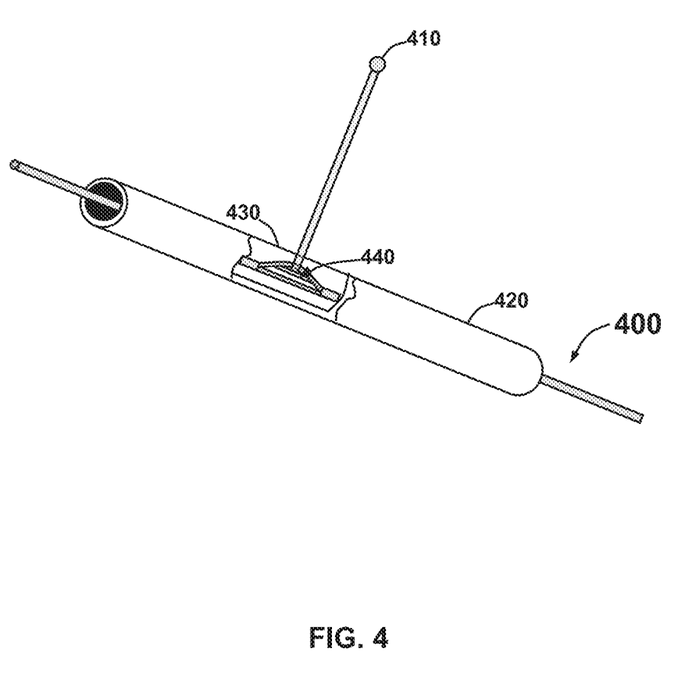
FIG. 4 illustrates a perspective view of a nerve leading to a target skeletal muscle in association with a single electrode, in accordance with the disclosed embodiments.

FIG. 4 illustrates a perspective view of a nerve 400 leading to a target skeletal muscle 180 in association with a signal electrode 410, in accordance with the disclosed embodiments. The electrode 410 can be configured in association with the nerve 400 utilizing a catheter 420. In general, the catheter 420 can be a tube inserted into a body cavity, duct, or vessel to thereby permit drainage, injection of fluids, or access by surgical instruments. The process of inserting the catheter 420 is catheterization. The catheter 420 can be a thin, flexible tube, though in some uses, it is a larger, solid catheter. The catheter 420 left inside the body, either temporarily or permanently, may be referred to as an indwelling catheter. A permanently inserted catheter 420 may be referred to as a permcath.

The neuro-coded signals 170 can be transmitted to the subject 110 via a constant voltage method. In the constant voltage method, the signal electrode 410 can be attached to the nerve 400 associated with the subject 110 that is to be stimulated. The signal electrode 410 is capable of providing both the positive and negative portions of the neuro-coded signals 170. The system 100 can only utilize the positive portion of the neuro-coded signal 170 for stimulating the nerve 400. The constant voltage method is based on the magnetic properties of the electrode 410 and the nerve 400 associated with the subject 110. The skeletal nerve 400 can be, for example, phrenic nerve that includes an efferent bundle 430 and an afferent bundle 440.

The electrode 410 can be placed in association with the nerve 400 by separating the efferent bundle 430 from the afferent bundle 440. The electrode 410 can be coated with an insulator in order to permit further insulation. The gradation of the muscle movement can be accomplished by slight or great changes in applied neuro-coded voltage. The electrode 410 can be attached or implanted to intersect with multiple nerves which are active in the control of muscle or system of muscles 180 required by quadriplegic or paraplegic patients to provide locomotion or any skeletal muscle activity for any purpose deemed to be useful in medical treatment of the subject 100. The electrode 410 can be in the form of a rod, flat, wire or any appropriate shape that is capable of receiving broadcasted neuro-coded signals from the electronic device 120. The voltage changes in the electronic device 120 can cause movement in the skeletal muscle 180 that is proportional to higher or lower voltage. For example, the neuro-coded signal 170 delivered at a slightly higher voltage can cause a stronger and larger muscle movement. Similarly, the neuro-coded signal 170 delivered at a lower voltage can cause a less or smaller movement of the target muscle.

Figure 5:
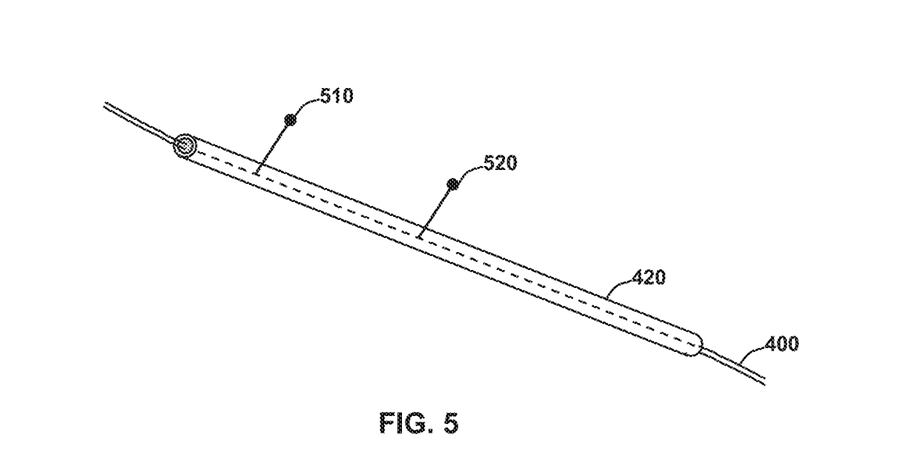
FIGS. 5-6 illustrate a perspective view of the nerve leading to the target skeletal muscle in association with a couple of electrodes, in accordance with the disclosed embodiments.
Figure 6:
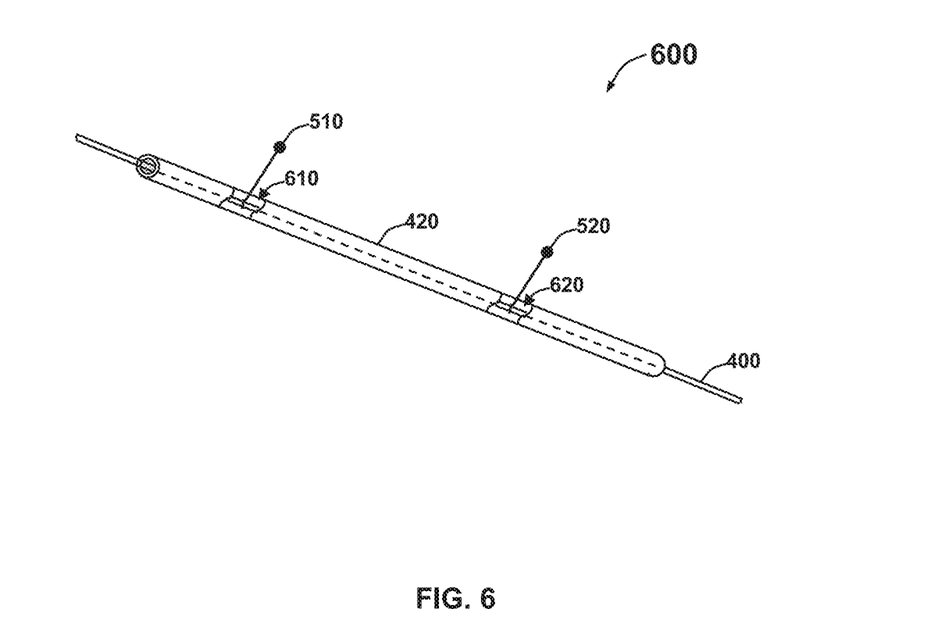

FIGS. 5-6 illustrate a perspective view of the nerve 400 leading to the target skeletal muscle 180 in association with a couple of electrodes 510 and 520, in accordance with the disclosed embodiments. The constant current method requires that a positive and a negative electrode 510 and 520 are attached to the nerve 400 associated with the skeletal muscle 180 to be stimulated. The distance between the electrodes 510 and 520 can be, for example, 2 cm and a ground connection can be made between the interior muscles 180 and an earth ground. Electrical grounding mats or grounding straps can be generally employed to ground the muscle 180 in order to minimize electrical noise and make handing of the nerve signals more exact. Note that the grounding straps, mats, and any other grounding connections with respect to the system 100 can be electrically connected to the same ground for obtaining proper results with respect to the functioning of the muscles 180.

The electrodes 510 and 520 can be implanted into the nerve 400 of the subject 110 via a keyhole surgical entrance. The electrodes 510 and 520 can be inserted at an appropriate level of any technically appropriate area or point such as points 610 and 620 of the nerve 400 to make specific attachment or synapse point required for treatment. The full length of the catheter 420 can be split and sewn back together once the electrodes 510 and 520 and the nerve loop are in place. The muscle contraction force and rate can be further controlled by the neuro-coded signals 170 generated by the electronic device 120. The electrodes 510 and 520 can be directly implanted on the nervous system of the selected muscle or muscle ganglion in order to transmit the signals to control the muscle function. Such implementation of the electrodes 510 and 520 can be pre-synaptic or post-synaptic.

The neuro-coded signal 170 associated with the subject 110 can include a preferred neuro-electrical code to accomplish smooth naturally expected muscle movement in the subject 110. An improper code in the subject 110 can tend to cause a harsh or unnatural muscle movement. The operative neuro-coded signals 170 can be similar to naturally produced signals from brain structures of the subject 110 for balancing and controlling varying operations such as, for example, but not limited to, bending, pulling, lifting, stretching, twisting or other bilateral or singular muscular actions of the shoulder, arm, leg, and fingers, etc.

The system 100 modulates the neuro-coded signals 170 so as to fine-tune muscle movements in the subject 110. The voltage levels for the neuro-coded signals 170 may not exceed 1 amp in its output electrical energy for each channel of the signal. Note that the system 100 can employ up to 10 or more channels simultaneously to exert waveform signals 170 to aid the subject 110 in moving or performing muscular tasks. The neuro-coded signals 170 can be electrically enlarged or reduced as to respective amplitudes and repetitive frequencies. The electrical or mechanically induced noise in the signal employed for treating muscle disorders can be electrically filtered, cleaned, or modified to be more exact in appearance just like the natural codes. The actual signal 170 collected from the muscle of a human or animal that is not impaired can be made available to an impaired patient.

The system and method disclosed herein can therefore control skeletal muscles by means of the neuro-coded electrical signal that can be readily and effectively employed in the treatment of various skeletal muscle impairments and disorders, including involuntary muscle movement (e.g., spasms and muscle contractions) and partial or full loss of muscle movement or control resulting from spinal injuries, multiple sclerosis, cerebral palsy, radiation-induced nerve damage, stroke induced neuron damage, etc. Without departing from the spirit and scope of the embodiments, any person ordinarily skilled in the field can make various changes and modifications to the embodiments to adapt it to various usages and conditions.

Based on the foregoing, it can be appreciated that a variety of embodiments, preferred and alternative, are disclosed. For example, in an embodiment, a method for controlling skeletal muscles can be implemented, which includes the steps of collecting a plurality of neuro-coded signals that are naturally generated in a body and are operative in control of at least one skeletal muscle from a nervous network in order to thereafter store the plurality of neuro-coded signals in a database associated with an electronic device; directly attaching an implantable muscle control device having at least one electrode to an appropriate nerve leading to at least one target skeletal muscle associated with a subject; and selecting a neuro-coded signal from the plurality of neuro-coded signal in order to thereafter broadcast the neuro-coded signal to the implantable device associated with the subject via a neuro-code transmission approach in order to activate and regulate the at least one target skeletal muscle.

In another embodiment, the aforementioned neuro-code transmission approach can be a constant voltage approach. In another embodiment, the aforementioned neuro-code transmission approach can be a constant current approach. In yet another embodiment, a step can be implemented for attaching a positive probe and a negative probe to the nerve or other connecting point on the body, so that the current supplied by the electronic device is consistent and repeatable throughout the delivery of the neuro-coded signal and a voltage level fluctuates as resistance changes. In still another embodiment, a step can be implemented for attaching a signal probe to the nerve that is capable of providing a positive and a negative portion of the neuro-coded signal wherein the positive portion stimulates the nerve.

In other embodiments, a step can be implemented for providing a ground connection between an interior muscle and an earth ground. In another embodiment, a step can be implemented for recording the neuro-coded signal that operate a sciatic nerve associated with a leg to thereby activate the target muscle of the leg via the neuro-coded signal. In still another embodiment, a step can be implemented for electrically varying the frequency and the amplitude of the neuro-coded signal so as to cause various movements in order to meet the demand of the nervous network. In yet other embodiments, a step can be implemented for attaching the implantable device to the appropriate nerve in a surgical process so as to arrive in close proximity of the target muscle. In still another embodiment, the at least one target muscle can comprise, for example, a shoulder muscle, an arm muscle, a hand muscle, a finger muscle, a leg muscle, etc.

In another embodiment, a system for controlling skeletal muscles can be implemented. Such a system can include, for example, an electronic device in association with a database to collect and store a plurality of neuro-coded signals that are naturally generated in a body and which can be reprogrammed and are operative in control of a skeletal muscle from a nervous network; an implantable muscle control device having at least one electrode directly attached to an appropriate nerve leading to at least one target skeletal muscle associated with a subject; and a neuro-code transmission means to broadcast a neuro-coded signal selected from the plurality of neuro-coded signals to the implantable device associated with the subject in order to activate and regulate the affected target skeletal muscle.

In another embodiment of such a system, a positive probe and a negative probe can be attached to the nerve so that a voltage level fluctuates as resistance changes. In yet another embodiment, such a system can include a signal probe that is capable of providing a positive and a negative portion of the neuro-code signal wherein the positive portion stimulates the nerve.

In another embodiment, a method for controlling skeletal muscles can be implemented, which includes, for example, the steps of collecting a plurality of neuro-coded signals that are naturally generated in a body and are operative in control of at least one skeletal muscle from a nervous network in order to thereafter store the plurality of neuro-coded signals in a database associated with an electronic device; directly attaching an implantable muscle control device having at least one electrode to an appropriate nerve leading to at least one target skeletal muscle associated with a subject; and selecting a neuro-coded signal from the plurality of neuro-coded signal in order to thereafter broadcast the neuro-coded signal to the implantable device associated with the subject via a neuro-code transmission approach in order to activate and regulate the at least one target skeletal muscle, the neuro-code transmission approach comprising a constant voltage approach or a constant current approach.

In another embodiment of such a method, a step can be implemented for providing a ground connection between an interior muscle and an earth ground. In yet another embodiment, a step can be implemented for recording the neuro-coded signal that operate a sciatic nerve associated with a leg to thereby activate the target muscle of the leg via the neuro-coded signal. In still another embodiment, a step can be implemented for electrically varying frequency and amplitude of the neuro-coded signal so as to cause various movements in order to meet the demand of the nervous network. In yet another embodiment, a step can be provided for attaching the implantable device to the appropriate nerve in a surgical process so as to arrive in dose proximity of the target muscle.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A method for controlling skeletal muscles, comprising:
    collecting a plurality of neuro-coded signals that are naturally generated in a body and are operative in control of at least one skeletal muscle from a nervous network, wherein an electronic device is associated with a neuro code signaling module associated with a database;
    storing said plurality of neuro-coded signals in said database associated with said electronic device;
    directly attaching an implantable muscle control device having at least one electrode to an appropriate nerve leading to at least one target skeletal muscle associated with a subject;
    selecting a neuro-coded signal from said plurality of neuro-coded signals;
    modulating said neuro-coded signal via said neuro-code signaling module to fine-tune muscle movements with respect to said at least one target skeletal muscle; and
    broadcasting said neuro-coded signal to said implantable device associated with said subject via said neuro-code transmission approach to thereby activate and regulate said at least one target skeletal muscle.

2. The method of claim 1 wherein said neuro-coded signal includes a plurality of channels and wherein said neuro-code transmission approach comprises a constant voltage approach wherein voltage levels for said neuro-coded signal do not exceed 1 amp in output electrical energy for each channel of said plurality of channels of said neuro-coded signal.

3. The method of claim 2 further comprising:
    attaching a signal probe to said nerve that is capable of providing a positive and a negative portion of said neuro-coded signal wherein said positive portion stimulates said nerve; and
    employing said plurality of channels of said neuro-coded signal simultaneously to exert said neuro-coded signal to aid in a movement or a performance of a muscular task by said at least one target skeletal muscle.

4. The method of claim 2 wherein said at least one target muscle comprises at least one of the following types of muscles:
    a shoulder muscle;
    an arm muscle;
    a hand muscle;
    a finger muscle; and
    a leg muscle.

5. The method of claim 1 wherein said neuro-code transmission approach comprises a constant current approach.

6. The method of claim 5 further comprising attaching a positive probe and a negative probe to said nerve or other connecting point on said body, so that current supplied by said electronic device is consistent and repeatable throughout the delivery of said neuro-coded signal and a voltage level fluctuates as resistance changes.

7. The method of claim 1 further comprising providing a ground connection between an interior muscle and an earth ground.

8. The method of claim 1 further comprising electrically varying frequency and amplitude of said neuro-coded signal so as to cause various movements in order to meet the demand of said nervous network.

9. The method of claim 1 further comprising attaching said implantable device to said appropriate nerve in a surgical process so as to arrive in close proximity of said at least one target skeletal muscle.

10. The method of claim 1 further comprising:
    providing a ground connection between an interior muscle and an earth ground, wherein voltage levels for said neuro-coded signal do not exceed 1 amp in output electrical energy for each channel of said neuro-coded signal; and
    electrically filtering, cleaning or modifying electrical noise and/or mechanically induced noise in said neuro-coded signal so that said neuro-coded signal will be more exact in appearance like a natural signal produced by a body.

11. The method of claim 10 further comprising attaching said implantable device to said appropriate nerve in a surgical process so as to arrive in close proximity of said at least one target skeletal muscle.

12. The method of claim 11 wherein said at least one target muscle comprises a muscle selected from a group of muscles comprising:
    a shoulder muscle;
    an arm muscle;
    a hand muscle;

a finger muscle; and
a leg muscle.

13. A system for controlling skeletal muscles, comprising:
an electronic device in association with a database to collect and store a plurality of neuro-coded signals that are naturally generated in a body and which can be reprogrammed and are operative in control of a skeletal muscle from a nervous network;
a neuro-code signaling module associated with said electronic device and said database;
an implantable muscle control device having at least one electrode directly attached to an appropriate nerve leading to at least one target skeletal muscle associated with a subject;
a modulation means for modulating said neuro-coded signal to fine-tune muscle movements with respect to said at least one target skeletal muscle;
a filter that communicates with said neuro-code signaling module and which electrically filters, cleans or modifies electrical noise and/or mechanically induced noise in said neuro-coded signal so that said neuro-coded signal will be more exact in appearance like a natural signal; and
a neuro-code transmission means to broadcast a neuro-coded signal selected from said plurality of neuro-coded signals to said implantable device associated with said subject in order to activate and regulate said affected target skeletal muscle.

14. The system of claim 13 further comprising a positive probe and a negative probe attached to said nerve so that a voltage level fluctuates as resistance changes.

15. The system of claim 13 further comprising a signal probe that is capable of providing a positive and a negative portion of said neuro-code signal wherein said positive portion stimulates said nerve.

16. A method for controlling skeletal muscles, said method comprising:
collecting a plurality of neuro-coded signals that are naturally generated in a body and are operative in control of at least one skeletal muscle from a nervous network;
storing said plurality of neuro-coded signals in a database associated with an electronic device associated with a neuro-code signaling module and said database;
directly attaching an implantable muscle control device having at least one electrode to an appropriate nerve leading to at least one target skeletal muscle associated with a subject; and
selecting a neuro-coded signal from said plurality of neuro-coded signal;
modulating said neuro-coded signal via said neuro-code signaling module to fine-tune muscle movements with respect to said at least one target skeletal muscle; and
thereafter broadcasting said neuro-coded signal to said implantable device associated with said subject via a neuro-code transmission approach in order to activate and regulate said at least one target skeletal muscle, said neuro-code transmission approach comprising a constant voltage approach or a constant current approach.

17. The method of claim 16 further comprising electrically varying frequency and amplitude of said neuro-coded signal so as to cause various movements in order to meet the demand of said nervous network.

18. The method of claim 17 wherein said at least one target muscle comprises at least one of the following types of muscles:
a shoulder muscle;
an arm muscle;
a hand muscle;
a finger muscle; and
a leg muscle.

* * * * *